(12) United States Patent
Schachar

(10) Patent No.: US 7,416,560 B1
(45) Date of Patent: Aug. 26, 2008

(54) SCLERAL PROSTHESIS FOR TREATMENT OF PRESBYOPIA AND OTHER EYE DISORDERS

(75) Inventor: Ronald A. Schachar, Dallas, TX (US)

(73) Assignee: Refocus Ocular, Inc., Dallas, TX (US)

( * ) Notice: Subject to any disclaimer, the term of this patent is extended or adjusted under 35 U.S.C. 154(b) by 1427 days.

(21) Appl. No.: 09/589,626

(22) Filed: Jun. 7, 2000

Related U.S. Application Data

(60) Provisional application No. 60/138,105, filed on Jun. 7, 1999.

(51) Int. Cl.
*A61F 2/14* (2006.01)
*A61F 9/013* (2006.01)

(52) U.S. Cl. ..................................................... 623/4.1

(58) Field of Classification Search ................... 623/4.1, 623/FOR. 113
See application file for complete search history.

(56) References Cited

U.S. PATENT DOCUMENTS

| 3,064,643 | A |   | 11/1962 | Dixon |
|---|---|---|---|---|
| 4,521,210 | A | * | 6/1985 | Wong ........................ 623/4.1 |
| 4,961,744 | A |   | 10/1990 | Kilmer et al. |
| 4,976,719 | A |   | 12/1990 | Siepser |
| 5,323,788 | A | * | 6/1994 | Silvestrini et al. .......... 623/5.12 |
| 5,354,331 | A | * | 10/1994 | Schachar .................... 623/4.1 |

FOREIGN PATENT DOCUMENTS

| FR |   | 2 784 287 | 4/2000 |
|---|---|---|---|
| WO |   | WO 96/40005 | 12/1996 |
| WO |   | WO 98/42409 | 10/1998 |

OTHER PUBLICATIONS

Spencer P. Thornton, "Anterior Ciliary Sclerotomy (ACS), A Procedure to Reverse Presbyopia", Surgery for Hyperopia and Presbyopia, 1997, pp. 33-36.
Ronald A. Schachar, MD, PhD, "Cause and Treatment of Presbyopia with a Method for Increasing the Amplitude of Accommodation", Annals of Ophthalmology, Dec. 1992, pp. 445-447, 452.

* cited by examiner

*Primary Examiner*—David H. Willse

(57) ABSTRACT

Presbyopia may be treated by implanting a scleral prosthesis within a plurality of elongated pockets formed in the tissue of the sclera of the eye. The implanted prosthesis exerts traction on the sclera in the region overlying the ciliary body which expands the sclera and the underlying ciliary body. This restores the effective working distance of the ciliary muscle and increases the amplitude of accommodation. A prosthesis of the present invention that contacts the sclera of an eyeball comprises a body having a first end and a second end. The body has (i) a planform for expanding the contacted sclera to increase the effective working distance of the ciliary muscle of the eyeball, and (ii) a structure that stabilizes the prosthesis within the surgically formed pocket within the sclera of the eyeball.

11 Claims, 3 Drawing Sheets

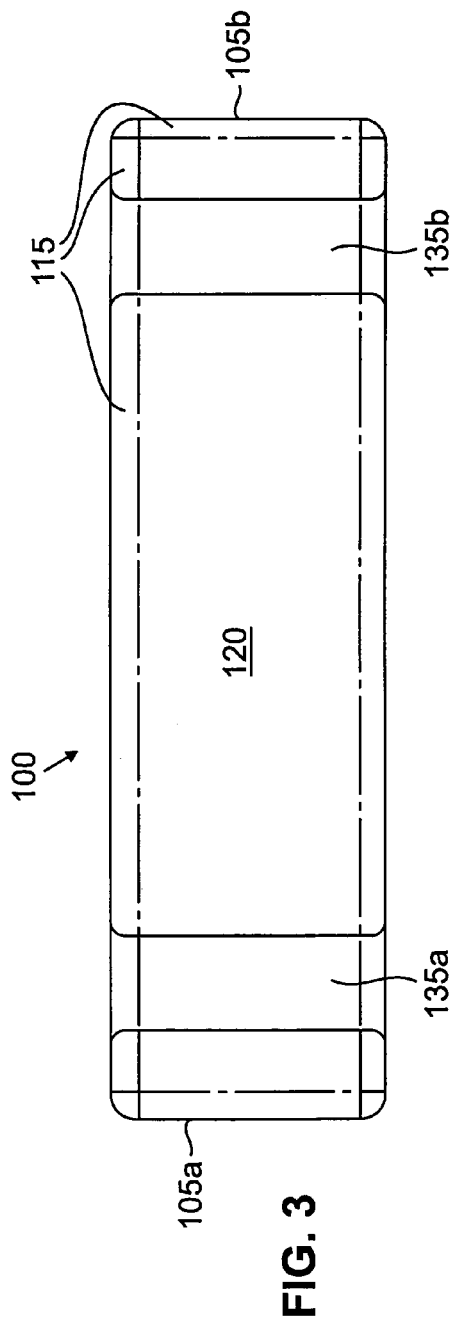
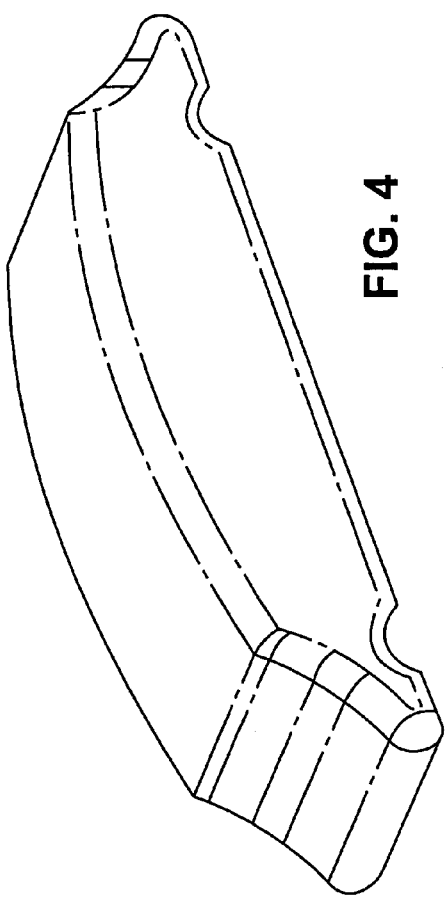

SCLERAL PROSTHESIS FOR TREATMENT OF PRESBYOPIA AND OTHER EYE DISORDERS

CROSS REFERENCE TO RELATED APPLICATIONS

The present invention is related to that disclosed in (1) U.S. patent application Ser. No. 08/946,975 entitled "SCLERAL PROSTHESIS FOR TREATMENT OF PRESBYOPIA AND OTHER EYE DISORDERS," filed Oct. 8, 1997, now U.S. Pat. No. 6,007,578 issued Dec. 28, 1999 (the "'975 Application"); (2) U.S. patent application Ser. No. 09/061,168 entitled "SCLERAL PROSTHESIS FOR TREATMENT OF PRESBYOPIA AND OTHER EYE DISORDERS," filed on Apr. 16, 1998, now U.S. Pat. No. 6,280,468 (a Continuation-in-Part Patent Application of the '975 Application); (3) U.S. patent application Ser. No. 09/472,535 entitled "SCLERAL PROSTHESIS FOR TREATMENT OF PRESBYOPIA AND OTHER EYE DISORDERS," filed Dec. 27, 1999, now U.S. Pat. No. 6,299,640 (a Continuation Patent Application of the '975 Application); and (4) U.S. Provisional Application No. 60/138,105 entitled "IMPROVED SCLERAL PROSTHESIS FOR TREATMENT OF PRESBYOPIA AND OTHER EYE DISORDERS," filed Jun. 7, 1999 (the specification of the present invention claims priority to this provisional application under 35 U.S.C. §119(e)(1)). All four patent documents, and the inventions disclosed therein, are commonly assigned to the assignee of the present invention, share common inventorship, and are incorporated herein by reference for all purposes as if fully set forth herein.

TECHNICAL FIELD OF THE INVENTION

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle.

BACKGROUND OF THE INVENTION

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary muscle, a muscular ring of tissue, located just within the outer supporting structure of the eye, the sclera. The ciliary muscle is relaxed in the unaccommodated eye and therefore assumes its largest diameter. According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision for distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings and/or segments have been used in ocular surgery for various purposes. Rings and/or segments of flexible and/or elastic material, attached or prepared in situ by fastening the ends of strips of the material around the posterior portion of the globe, posterior to the pars plana (over the underlying retina), have been used to compress the sclera in certain posterior regions. Supporting rings of metal, adapted to fit the contour of the sclera have been used as temporary supporting structures during surgery on the globe. However, none of these known devices have been used for surgical treatment of presbyopia, and none have been adapted to the special needs of prosthetic devices used in treating presbyopia.

Accordingly, a need has continued to exist for a method of treating presbyopia that will increase the amplitude of accommodation of the presbyopic eye, thereby lessening or eliminating the need for auxiliary spectacle lenses to relieve the problems of presbyopia.

SUMMARY OF THE INVENTION

Presbyopia and other eye disorders are treated by implanting within a plurality of elongated pockets formed in the tissue of the sclera of the eye transverse to a meridian of the eye, a prosthesis having an elongated base member having an inward surface adapted to be placed against the inward wall of the pocket and having a ridge on the inward surface of the base extending along at least a major portion of the major dimension of the base. The combined effect of the implanted prostheses is to exert a radially outward traction on the sclera in the region overlying the ciliary body which expands the sclera in the affected region together with the underlying ciliary body. The expansion of the ciliary body restores the effective working distance of the ciliary muscle in the presbyopic eye and thereby increases the amplitude of accommodation. Introduced is an improved scleral prosthesis for the treatment of presbyopia and other eye disorders. An exemplary prosthesis in accordance with the teachings hereof is adapted for contact with the sclera of an eyeball, and comprises a body having a first end and a second end wherein the body has (i) a planform adapted to expand the contacted sclera to increase the effective working distance of the ciliary muscle of the eyeball, and (ii) means for stabilizing the prosthesis within the surgically formed pocket within the sclera of the eyeball.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

BRIEF DESCRIPTION OF THE DRAWINGS

An advantageous embodiment of the present invention may be understood with reference to the following descriptions taken in conjunction with the accompanying drawings, wherein like numbers designate like objects, in which:

FIG. 3 illustrates a bottom plan view of the embodiment of the scleral prosthesis of FIGS. 1 and 2;

FIG. 4 illustrates a top-side isometric view of the embodiment of the scleral prosthesis of FIGS. 1 to 3;

DETAILED DESCRIPTION OF THE INVENTION

Figure 1:
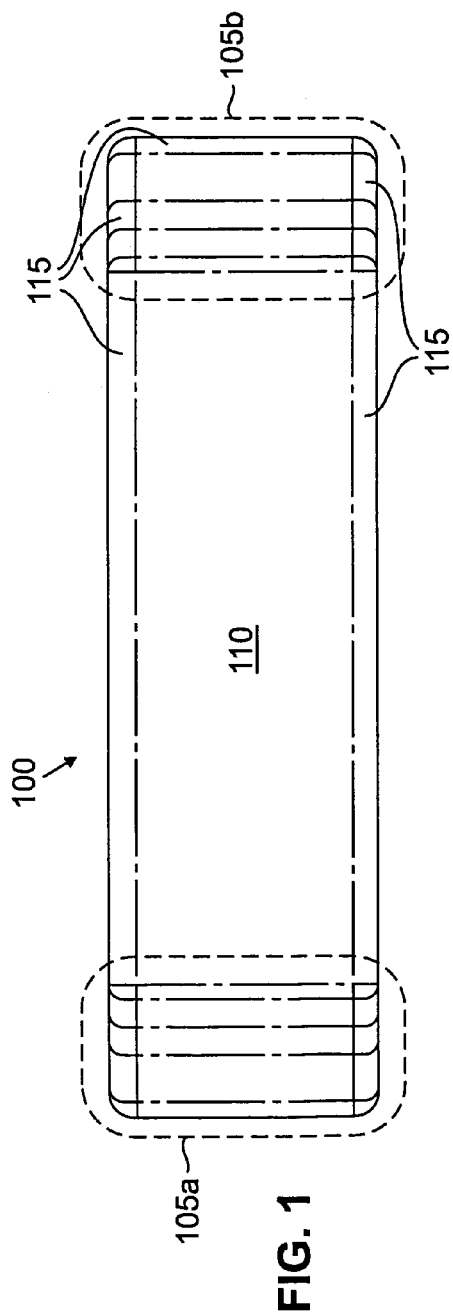
FIG. 1 illustrates a top plan view of an advantageous embodiment of an improved scleral prosthesis in accordance with the principles of the present invention.

The principles of the present invention introduce and teach improvements upon the scleral prosthesis introduced and taught in U.S. patent application Ser. No. 08/946,975 entitled "SCLERAL PROSTHESIS FOR TREATMENT OF PRESBYOPIA AND OTHER EYE DISORDERS," filed Oct. 8, 1997 (the "'975 application"); U.S. patent application Ser. No. 09/061,168 entitled "SCLERAL PROSTHESIS FOR TREATMENT OF PRESBYOPIA AND OTHER EYE DISORDERS," filed on Apr. 16, 1998 (a Continuation-in-Part patent application of the '975 application); U.S. patent application Ser. No. 09/472,535 entitled "SCLERAL PROSTHESIS FOR TREATMENT OF PRESBYOPIA AND OTHER EYE DISORDERS," filed Dec. 27, 1999 (a Continuation patent application of the '975 application); and U.S. Provisional Application No. 60/138,105 entitled "IMPROVED SCLERAL PROSTHESIS FOR TREATMENT OF PRESBYOPIA AND OTHER EYE DISORDERS," filed Jun. 7, 1999 (the specification of the present invention claims priority to this provisional application under 35 U.S.C. §119(e) (1)). All four patent documents, and the inventions disclosed therein, are commonly assigned to the assignee of the present invention, share common inventorship, and are incorporated herein by reference for all purposes as if fully set forth herein.

According to certain of the inventions introduced and taught in the above-incorporated patent documents, presbyopia, and certain other eye disorders (e.g., hyperopia, primary open angle glaucoma, ocular hypertension, etc.), may suitably be treated by increasing the effective working distance of the ciliary muscle. This may be accomplished by increasing the distance between the ciliary muscle and the lens equator, preferably by increasing the diameter of the sclera (i.e., scleral expansion) in the region of the ciliary body.

According to an advantageous embodiment, the effective working distance of the ciliary muscle may suitably be increased by implanting, within pockets surgically formed in the sclera of the eye, a plurality of prostheses designed to place an outward traction on the sclera in the region of the ciliary body. Each prosthesis comprises an elongated base having a first end and a second end and one of a ridge or a crest. The implanted prosthesis applies an outward force on the scleral pocket to elevate the portion of the sclera attached thereto to increase the effective working distance of the ciliary muscle of the eyeball. The plurality of prostheses are therefore designed to apply an outwardly directed force to the sclera cooperatively.

An advantageous embodiment of the prosthesis of the invention disclosed in the above-incorporated patent documents has a substantially circumferential body. The circumferential body has a top surface that is adapted for placement against the outer wall of the pocket surgically formed in the sclera, applying an outward force thereto.

Unfortunately, due to its circumferential body shape, a bottom surface of the prosthesis has limited surface contact with the inner wall of the surgically formed scleral pocket, generally in the area of the first and second ends thereof. Due, at least in part, to the disproportionate surface contact of the top surface relative to the bottom surface of the body of the prosthesis, the prosthesis tends: (i) to slide back and forth within the scleral pocket causing the same to be less effective in treating presbyopia, and (ii) to turn or to topple over within the scleral pocket causing the same be substantially ineffective in treating presbyopia.

Turning initially to FIG. 1, illustrated a top plan view of an advantageous embodiment of an improved scleral prosthesis in accordance with the principles of the present invention. To overcome the above-identified deficiencies of the circumferential body prosthesis, the improved prosthesis of the present invention comprises a body (generally designated 100), having a first end and a second end (generally designated 105a and 105b, respectively), that is adapted to expand a contacted sclera to increase the effective working distance of the ciliary muscle of the eyeball while providing means for stabilizing the prosthesis relative to the contacted sclera. As used herein the term "end" or "ends" refers to an end that is unattached to, and not in contact with, other portions of the prosthesis body, such as the other end 105a or 105b or a central portion of the body 100 between those ends. Ends 105a and 105b are thus spaced apart from one another, and are not looped around past each other such that body 100 forms a continuous band. The body 100 includes a top surface 110 that may suitably be adapted to contact ocular tissue within a pocket (or loop) surgically formed within the sclera of the eyeball. Surgical procedures for suitably forming an appropriate scleral pocket are described in the above-incorporated patent documents and further discussion is not necessary for the purposes of this patent document. Exemplary top surface 110 is illustratively shown having a convex planform.

Top surface includes a perimeter 110 that, according to the illustrated embodiment, has a convex, sloped, or otherwise non-sharp edge to avoid cutting, tearing or otherwise damaging the sclera, particularly the surgically formed scleral pocket. It should be noted that the first and second ends 105a,b of body 100 illustratively include a more pronounced slope relative to the remainder of top surface 110 (described in greater detail below).

Figure 2:
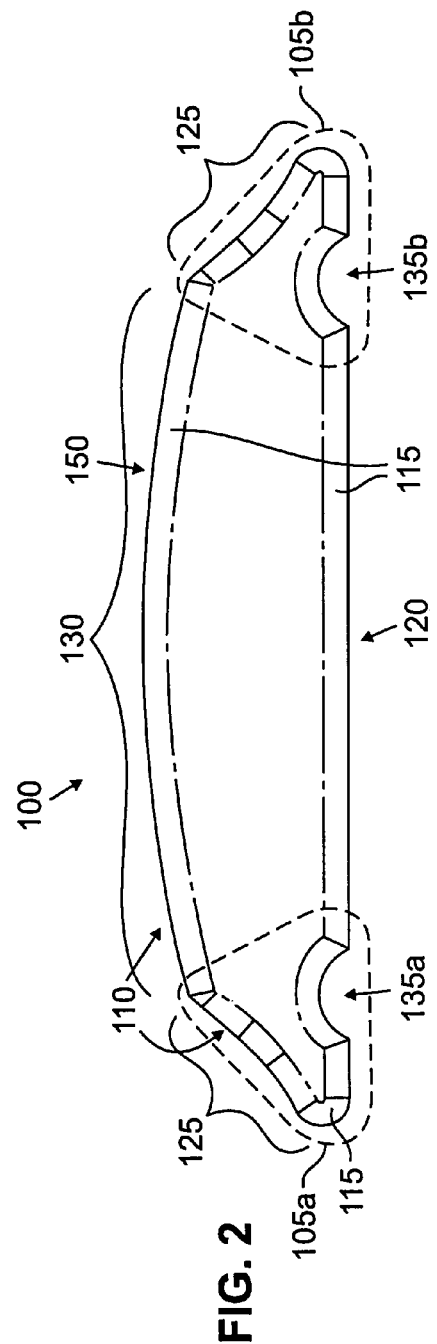
FIG. 2 illustrates a side elevational view of the embodiment of the scleral prosthesis of FIG. 1.

FIG. 2 illustrates a side elevational view of the embodiment of the scleral prosthesis of FIG. 1. The prosthesis body 100 again has first and second ends 105a,b, top surface 110, non-sharp edges 115 and a bottom surface 120. Exemplary bottom surface 120 is illustratively shown having a substantially straight planform relative to top surface 110. Preferably, bottom surface 120 is wider than the maximum height of prosthesis body 100.

It should be noted that the exemplary shapes of top surface 110 and bottom surface 120 are provided for illustrative purposes only. Those of skill in the art will understand that body 100 may have any shape suitably adapted, via a cooperation among the shapes of the surfaces of the body, to exert an outward force on the scleral pocket to elevate the portion of the sclera attached thereto to increase the effective working distance of the ciliary muscle of the eyeball, whether such surface is convex, concave, circumferential or otherwise.

It should be further noted that advantageous and exemplary dimensions of body 100 are provided, again for illustrative purposes. Any suitable body planform of dimensions appropriate and in accordance with the principles of the present invention may be used. To that end, exemplary first and second ends 105a,b, in cooperation with top and bottom surfaces 110, 120, provide a means for stabilizing the prosthesis within a surgically formed pocket within the sclera of the eyeball, enabling prosthesis body 100 to substantially permanently exert an outward force on the scleral pocket to elevate the portion of the sclera attached thereto to increase the effective working distance of the ciliary muscle.

To that end, exemplary bottom surface 120 is adapted for increased surface contact with the ocular tissue within the surgically formed pocket relative to the prior embodiments of the prosthesis of the above-incorporated patent documents. This increased ocular surface tissue contact at least substantially eliminates turning over, toppling over or otherwise rotating of the prosthesis body within the scleral pocket thereby ensuring effective treatment of presbyopia.

Bottom surface 120 surface may suitably be adapted to contact an amount of ocular tissue that is at least substantially equal to an amount of ocular tissue contacted by top surface 100 within the surgically formed scleral pocket. In alternate embodiments, this relationship may be altered based upon the planform of body 100. For instance, the area of bottom surface 120 may suitably be greater than the area of top surface 110.

Turning to first and second ends 105a,b, each exemplary end is adapted to fix body 100 within a surgically formed pocket through a physical combination/cooperation of (I) a sloping minor portion 125 of top surface 110 relative to a major portion 130 of top surface 110, and (ii) a groove 135. This exemplary physical combination/cooperation at least substantially fixes body 100 within a surgically formed pocket within the scleral pocket thereby ensuring effective treatment of presbyopia.

It should be noted that although first and second ends 105a,b have a partially concave portion 125 of top surface 110 and grooves 135a,b provide a partially concave bottom surface 120, alternate embodiments may include at least one end 105 that has a partially convex top surface, or bottom surface 120 that may suitably include at least one portion that is at least partially convex.

Regardless, the physical cooperation among the various dimensions and characteristics (e.g., smooth, coarse, finished, polished, etc.) of the surfaces and ends of prosthesis body 100, suitable means for stabilizing the same within a surgically formed pocket within the sclera of the eyeball.

Thus, the exemplary embodiment of FIGS. 1 and 2 illustrates advantageous features wherein top surface 110 starts with a concave surface 125 at first end 105a for approximately 750 microns and then moves smoothly to a smooth convex-like curve for four millimeters, and then to another concave surface 125 at second end 105b for approximately another 750 microns—for a total top surface length of 5.5 millimeters. The radius of curvature of the major convex surface is approximately 9 millimeters, the interconnecting curve has a radius of approximately 153 microns and the concave surface has a radius of approximately 500 microns. The concave surface forms a rounded portion having a radius of curvature of approximately 125 microns that connects to bottom surface 120. Bottom surface 120 has a straight part which extends for approximately 500 microns to a concavity that has a radius of curvature of approximately 500 microns and a height of approximately 150 microns. The concavity forms a groove illustratively extending through the whole bottom surface 120 of body 100. A major portion of bottom surface 120 extends approximately 3.5 millimeters between the first groove and a second groove (the second groove being substantially identical to the first groove).

Figure 5:
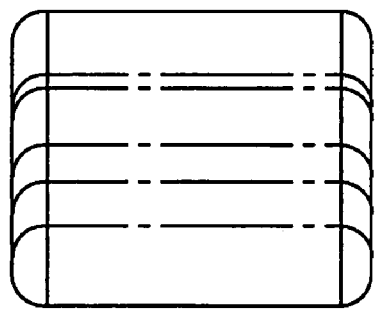
FIG. 5 illustrates a top plan view of one end of the embodiment of the scleral prosthesis of FIGS. 1 to 4.
Figure 6:
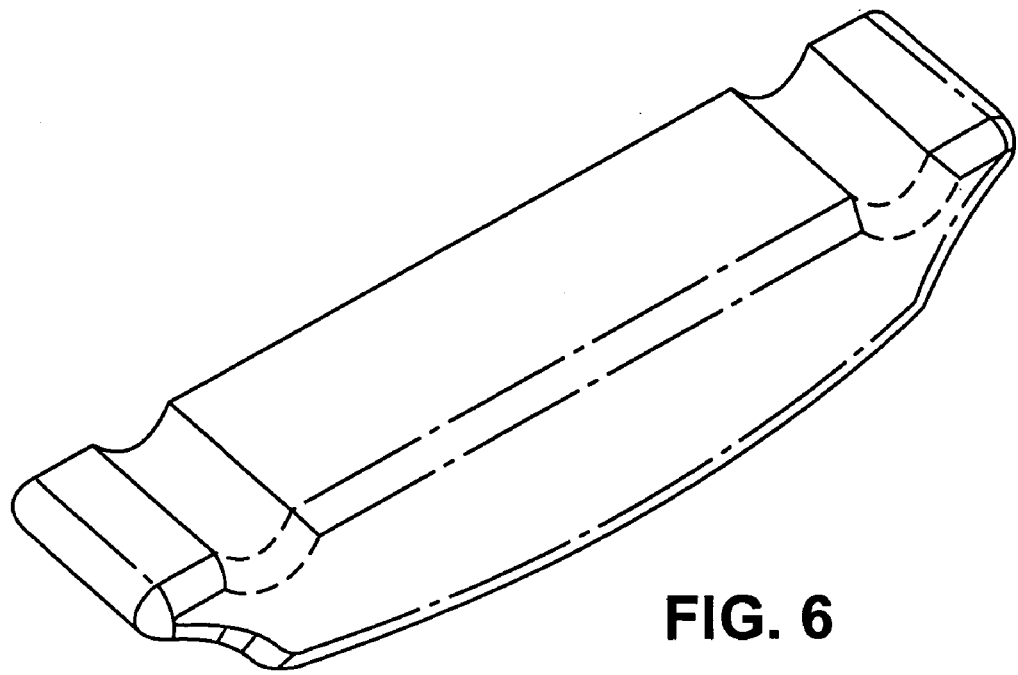
FIG. 6 illustrates a bottom-side isometric view of the embodiment of the scleral prosthesis of FIGS. 1 to 5.

Turning to FIG. 3, illustrated is an exemplary bottom plan view of the embodiment of the scleral prosthesis of FIGS. 1 and 2. It should again be noted that width, length, or other common dimensions need not be the same, meaning, for instance, that bottom surface 120 may suitably be larger in area than top surface 110. Turning to FIG. 4, illustrated is a top-side isometric view of the embodiment of the scleral prosthesis of FIGS. 1 to 3. Again, the exemplary non-sharp edges are shown. Turning to FIG. 5, illustrated is a top plan view of one end of the embodiment of the scleral prosthesis of FIGS. 1 to 4. Finally, turning to FIG. 6, illustrated is a bottom-side isometric view of the embodiment of the scleral prosthesis of FIGS. 1 to 5.

Other important features of the exemplary stabilizing means 105*a,b*, and 120 (in cooperation with top surface 110), of the illustrated embodiment, is that the width of body 100 is preferably larger than its maximum height—in previous prosthesis embodiments, width was not larger than the maximum height, and enabled turning over, etc. Further, bottom surface 120 is relatively flat except for grooves 135 or any other suitable means for fixing prosthesis body 100 within the scleral pocket (e.g., hooks, fasteners, clips, etc.). Exemplary grooves 135 therefore act to prevent prosthesis body 100 from sliding—grooves 135 may suitably be positioned in line with the incision to form the scleral pocket causing the incision to "curve up" as a result of the pressure into the groove, thereby preventing the prosthesis from sliding in either direction. Thirdly, first or second end 105*a,b* includes a concavity to facilitate ease of entrance into the scleral pocket.

In short, ends 105*a,b* cooperate to ease insertion into the scleral pocket and to fix the same once appropriately positioned therein. Alternate means for fixing, or, more globally, stabilizing the prosthesis include positioning a hole in the prosthesis body and suturing the same, gluing one or more surfaces of the same to scleral pocket, a plurality of scleral pockets (or loops).

Yet another advantage of having a total body mass or "thickness" is that the present prosthesis provides increased lift relative to prior embodiments disclosed in the above-incorporated patent documents, which is a primary object of the prostheses.

The foregoing prosthesis may be manufactured in accord with the methods set forth in the above-incorporated patent documents or otherwise known, may be from materials set forth in the above-incorporated patent documents or otherwise known, may be surgically implanted as set forth in the above-incorporated patent documents or as otherwise known, such as an injection wherein the prosthesis would be inserted and then possibly filled with fluid, plastic or otherwise (in an embodiment wherein the ends extend beyond the scleral pocket, the body of the prosthesis may be filled and the end(s) actually become wider than the incision, precluding movement), including, for instance, new metals.

The present invention has been described in detail. Those skilled in the art will understand that various changes, substitutions and alterations may be made herein without departing from the spirit and scope of the invention in its broadest form.

What is claimed is:

1. A prosthesis that contacts the sclera of an eyeball, said prosthesis comprising a body having a first end and a second end, said body having a planform that expands said contacted sclera to increase the effective working distance of the ciliary muscle of the eyeball;
    wherein said body further comprises a top surface that contacts ocular tissue within a pocket surgically formed within the sclera of the eyeball,
    wherein said body further comprises a means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially concave top surface.

2. A prosthesis that contacts the sclera of an eyeball, said prosthesis comprising a body having a first end and a second end, said body having a planform that expands said contacted sclera to increase the effective working distance of the ciliary muscle of the eyeball;
    wherein said body further comprises a top surface that contacts ocular tissue within a pocket surgically formed within the sclera of the eyeball,
    wherein said body further comprises a means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially convex top surface.

3. A prosthesis that contacts the sclera of an eyeball, said prosthesis comprising a body having a first end and a second end, said body having a planform that expands said contacted sclera to increase the effective working distance of the ciliary muscle of the eyeball;
    wherein said body further comprises a top surface that contacts ocular tissue within a pocket surgically formed within the sclera of the eyeball,
    wherein said body further comprises a means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially concave bottom surface.

4. A prosthesis that contacts the sclera of an eyeball, said prosthesis comprising a body having a first end and a second end, said body having a planform that expands said contacted sclera to increase the effective working distance of the ciliary muscle of the eyeball;
    wherein said body further comprises a top surface that contacts ocular tissue within a pocket surgically formed within the sclera of the eyeball,
    wherein said body further comprises a means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially convex bottom surface.

5. A prosthesis that contacts the sclera of an eyeball, said prosthesis comprising a body having a first end and a second end, said body having a planform that expands said contacted sclera to increase the effective working distance of the ciliary muscle of the eyeball and further means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially concave top surface.

6. A prosthesis that contacts the sclera of an eyeball, said prosthesis comprising a body having a first end and a second end, said body having a planform that expands said contacted sclera to increase the effective working distance of the ciliary muscle of the eyeball and further means for stabilizing said prosthesis within said surgically formed pocket within the sclera of the eyeball,
    wherein said stabilizing means includes at least one of said first end and said second end that fixes said body within said surgically formed pocket, and
    wherein said at least one of said first end and said second end has a partially convex top surface.

7. A prosthesis that contacts the sclera of an eyeball, said prosthesis comprising a body having a first end and a second end, said body having a planform that expands said contacted sclera to increase the effective working distance of the ciliary muscle of the eyeball and further means for stabilizing said prosthesis within said surgically formed pocket within the sclera of the eyeball, wherein said stabilizing means includes at least one of said first end and said second end that fixes said body within said surgically formed pocket, and wherein said at least one of said first end and said second end has a partially concave bottom surface.

8. A prosthesis that contacts the sclera of an eyeball, said prosthesis comprising a body having a first end and a second end, said body having a planform that expands said contacted sclera to increase the effective working distance of the ciliary muscle of the eyeball and further means for stabilizing said prosthesis within said surgically formed pocket within the sclera of the eyeball, wherein said stabilizing means includes at least one of said first end and said second end that fixes said body within said surgically formed pocket, and wherein said at least one of said first end and said second end has a partially convex bottom surface.

9. A prosthesis for contacting the sclera of an eyeball, said prosthesis comprising:

a body having at least one end portion which is wider than an incision forming a scleral pocket for containing said prosthesis, a remainder of said body extending from said at least one end portion in a direction substantially perpendicular to a width dimension of said at least one end portion, a bottom surface of said body having at least one concave region separated from an end of said body by a flat surface, said at least one concave region having a radius of curvature of approximately five hundred microns, whereby said prosthesis exerts an outward force on said scleral pocket to elevate a portion of the sclera attached thereto when said prosthesis is disposed within said scleral pocket, and wherein said at least one end portion is configured to extend beyond said scleral pocket.

10. The prosthesis as set forth in claim 9, wherein said body includes a major convex surface having a radius of curvature of approximately nine millimeters.

11. The prosthesis as set forth in claim 9, wherein end portions of said body are sloped.

* * * * *

UNITED STATES PATENT AND TRADEMARK OFFICE
CERTIFICATE OF CORRECTION

PATENT NO.         : 7,416,560 B1
APPLICATION NO. : 09/589626
DATED              : August 26, 2008
INVENTOR(S)       : Ronald A. Schachar It is certified that error appears in the above-identified patent and that said Letters Patent is hereby corrected as shown below:

Title page, item (*) Notice: patent term adjustment should read as follows:
NINE HUNDRED ELEVEN (911) DAYS.

Signed and Sealed this

Thirteenth Day of October, 2009

David J. Kappos
*Director of the United States Patent and Trademark Office*